US008199007B2

(12) United States Patent
Coakley et al.

(10) Patent No.: US 8,199,007 B2
(45) Date of Patent: Jun. 12, 2012

(54) FLEX CIRCUIT SNAP TRACK FOR A BIOMETRIC SENSOR

(75) Inventors: Joseph Coakley, Dublin, CA (US); George L. Matlock, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 643 days.

(21) Appl. No.: 12/345,397

(22) Filed: Dec. 29, 2008

(65) Prior Publication Data

US 2009/0168385 A1 Jul. 2, 2009

Related U.S. Application Data

(60) Provisional application No. 61/009,676, filed on Dec. 31, 2007.

(51) Int. Cl.
*A61B 5/00* (2006.01)

(52) U.S. Cl. .......... 340/540; 361/679.01; 361/807; 361/809; 340/573.1; 600/310; 600/483; 600/513

(58) Field of Classification Search .......... 600/310; 340/540
See application file for complete search history.

(56) References Cited

U.S. PATENT DOCUMENTS

| | | | |
|---|---|---|---|
| 3,482,565 A * | 12/1969 | Gowen | 600/480 |
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A * | 8/1987 | Goldberger et al. | 600/344 |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |

(Continued)

FOREIGN PATENT DOCUMENTS

DE 3516338 11/1986

(Continued)

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

(Continued)

*Primary Examiner* — Anthony Q Edwards
(74) *Attorney, Agent, or Firm* — Fletcher Yoder

(57) ABSTRACT

The present disclosure relates to a sensor assembly, comprising a frame comprising structural supports, and housings configured to house an optical component; and a strut disposed between one of the structural supports and housings; wherein the struts are adapted to house conductors connecting the optical component to a circuit.

5 Claims, 3 Drawing Sheets

U.S. PATENT DOCUMENTS

| | | | |
|---|---|---|---|
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A * | 7/1991 | Muz | 600/344 |
| 5,040,539 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H0001039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp, Jr. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A * | 8/1994 | Ivers et al. | 600/340 |
| 5,343,818 A | 9/1994 | McCarthy et al. | |
| 5,343,869 A | 9/1994 | Pross et al. | |
| 5,348,003 A * | 9/1994 | Caro | 600/310 |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |
| 5,417,207 A | 5/1995 | Young et al. | |
| 5,421,329 A | 6/1995 | Casciani et al. | |
| 5,425,360 A | 6/1995 | Nelson | |
| 5,425,362 A | 6/1995 | Siker et al. | |
| 5,427,093 A | 6/1995 | Ogawa et al. | |
| 5,429,128 A | 7/1995 | Cadell et al. | |
| 5,429,129 A | 7/1995 | Lovejoy et al. | |
| 5,431,159 A | 7/1995 | Baker et al. | |
| 5,431,170 A | 7/1995 | Mathews | |

| Patent No. | Kind | Date | Inventor(s) |
|---|---|---|---|
| 5,437,275 A * | | 8/1995 | Amundsen et al. ............ 600/323 |
| 5,438,986 A | | 8/1995 | Disch et al. |
| 5,448,991 A | | 9/1995 | Polson et al. |
| 5,452,717 A | | 9/1995 | Branigan et al. |
| 5,465,714 A | | 11/1995 | Scheuing |
| 5,469,845 A | | 11/1995 | DeLonzor et al. |
| RE35,122 E | | 12/1995 | Corenman et al. |
| 5,474,065 A | | 12/1995 | Meathrel et al. |
| 5,482,034 A | | 1/1996 | Lewis et al. |
| 5,482,036 A | | 1/1996 | Diab et al. |
| 5,483,646 A | | 1/1996 | Uchikoga |
| 5,485,847 A | | 1/1996 | Baker, Jr. |
| 5,490,505 A | | 2/1996 | Diab et al. |
| 5,490,523 A | | 2/1996 | Isaacson et al. |
| 5,491,299 A | | 2/1996 | Naylor et al. |
| 5,494,032 A | | 2/1996 | Robinson et al. |
| 5,497,771 A | | 3/1996 | Rosenheimer |
| 5,499,627 A | | 3/1996 | Steuer et al. |
| 5,503,148 A | | 4/1996 | Pologe et al. |
| 5,505,199 A | | 4/1996 | Kim |
| 5,507,286 A | | 4/1996 | Solenberger |
| 5,511,546 A * | | 4/1996 | Hon ............... 600/490 |
| 5,517,988 A | | 5/1996 | Gerhard |
| 5,520,177 A | | 5/1996 | Ogawa et al. |
| 5,521,851 A | | 5/1996 | Wei et al. |
| 5,522,388 A | | 6/1996 | Ishikawa et al. |
| 5,524,617 A | | 6/1996 | Mannheimer |
| 5,529,064 A | | 6/1996 | Rall et al. |
| 5,533,507 A | | 7/1996 | Potratz |
| 5,551,423 A | | 9/1996 | Sugiura |
| 5,551,424 A | | 9/1996 | Morrison et al. |
| 5,553,614 A | | 9/1996 | Chance |
| 5,553,615 A | | 9/1996 | Carim et al. |
| 5,555,882 A | | 9/1996 | Richardson et al. |
| 5,558,096 A | | 9/1996 | Palatnik |
| 5,560,355 A | | 10/1996 | Merchant et al. |
| 5,564,417 A | | 10/1996 | Chance |
| 5,575,284 A | | 11/1996 | Athan et al. |
| 5,575,285 A | | 11/1996 | Takanashi et al. |
| 5,577,500 A | | 11/1996 | Potratz |
| 5,582,169 A | | 12/1996 | Oda et al. |
| 5,584,296 A | | 12/1996 | Cui et al. |
| 5,588,425 A | | 12/1996 | Sackner et al. |
| 5,588,427 A | | 12/1996 | Tien |
| 5,590,652 A | | 1/1997 | Inai |
| 5,595,176 A | | 1/1997 | Yamaura |
| 5,596,986 A | | 1/1997 | Goldfarb |
| 5,611,337 A | | 3/1997 | Bukta |
| 5,617,852 A | | 4/1997 | MacGregor |
| 5,619,992 A | | 4/1997 | Guthrie et al. |
| 5,626,140 A | | 5/1997 | Feldman et al. |
| 5,630,413 A | | 5/1997 | Thomas et al. |
| 5,632,272 A | | 5/1997 | Diab et al. |
| 5,632,273 A | | 5/1997 | Suzuki |
| 5,634,459 A | | 6/1997 | Gardosi |
| 5,638,593 A | | 6/1997 | Gerhardt et al. |
| 5,638,818 A | | 6/1997 | Diab et al. |
| 5,645,060 A | | 7/1997 | Yorkey |
| 5,645,440 A | | 7/1997 | Tobler et al. |
| 5,660,567 A | | 8/1997 | Nierlich et al. |
| 5,662,105 A | | 9/1997 | Tien |
| 5,662,106 A | | 9/1997 | Swedlow et al. |
| 5,666,952 A | | 9/1997 | Fuse et al. |
| 5,671,529 A | | 9/1997 | Nelson |
| 5,673,692 A | | 10/1997 | Schulze et al. |
| 5,673,693 A | | 10/1997 | Solenberger |
| 5,676,139 A | | 10/1997 | Goldberger et al. |
| 5,676,141 A | | 10/1997 | Hollub |
| 5,678,544 A | | 10/1997 | DeLonzor et al. |
| 5,680,857 A | | 10/1997 | Pelikan et al. |
| 5,685,299 A | | 11/1997 | Diab et al. |
| 5,685,301 A | | 11/1997 | Klomhaus |
| 5,687,719 A | | 11/1997 | Sato et al. |
| 5,687,722 A | | 11/1997 | Tien et al. |
| 5,692,503 A | | 12/1997 | Kuenstner |
| 5,692,505 A | | 12/1997 | Fouts |
| 5,709,205 A | | 1/1998 | Bukta |
| 5,713,355 A | | 2/1998 | Richardson et al. |
| 5,724,967 A | | 3/1998 | Venkatachalam |
| 5,727,547 A | | 3/1998 | Levinson et al. |
| 5,731,582 A | | 3/1998 | West |
| 393,830 A | | 4/1998 | Tobler et al. |
| 5,743,260 A | | 4/1998 | Chung et al. |
| 5,743,263 A | | 4/1998 | Baker, Jr. |
| 5,743,349 A * | | 4/1998 | Steinberg ............... 180/272 |
| 5,746,206 A | | 5/1998 | Mannheimer |
| 5,746,697 A | | 5/1998 | Swedlow et al. |
| 5,752,914 A | | 5/1998 | DeLonzor et al. |
| 5,755,226 A | | 5/1998 | Carim et al. |
| 5,758,644 A | | 6/1998 | Diab et al. |
| 5,760,910 A | | 6/1998 | Lepper, Jr. et al. |
| 5,766,125 A | | 6/1998 | Aoyagi et al. |
| 5,766,127 A | | 6/1998 | Pologe et al. |
| 5,769,785 A | | 6/1998 | Diab et al. |
| 5,772,587 A | | 6/1998 | Gratton et al. |
| 5,774,213 A | | 6/1998 | Trebino et al. |
| 5,776,058 A | | 7/1998 | Levinson et al. |
| 5,776,059 A | | 7/1998 | Kaestle et al. |
| 5,779,630 A | | 7/1998 | Fein et al. |
| 5,779,631 A | | 7/1998 | Chance |
| 5,782,237 A | | 7/1998 | Casciani et al. |
| 5,782,756 A | | 7/1998 | Mannheimer |
| 5,782,757 A | | 7/1998 | Diab et al. |
| 5,782,758 A | | 7/1998 | Ausec et al. |
| 5,786,592 A | | 7/1998 | Hök |
| 5,790,729 A | | 8/1998 | Pologe et al. |
| 5,792,052 A | | 8/1998 | Isaacson et al. |
| 5,795,292 A | | 8/1998 | Lewis et al. |
| 5,797,841 A | | 8/1998 | DeLonzor et al. |
| 5,800,348 A | | 9/1998 | Kaestle |
| 5,800,349 A | | 9/1998 | Isaacson et al. |
| 5,803,910 A | | 9/1998 | Potratz |
| 5,807,246 A | | 9/1998 | Sakaguchi et al. |
| 5,807,247 A | | 9/1998 | Merchant et al. |
| 5,807,248 A | | 9/1998 | Mills |
| 5,810,723 A | | 9/1998 | Aldrich |
| 5,810,724 A | | 9/1998 | Gronvall |
| 5,813,980 A | | 9/1998 | Levinson et al. |
| 5,817,008 A | | 10/1998 | Rafert et al. |
| 5,817,009 A | | 10/1998 | Rosenheimer et al. |
| 5,817,010 A | | 10/1998 | Hibl |
| 5,818,985 A | | 10/1998 | Merchant et al. |
| 5,820,550 A | | 10/1998 | Polson et al. |
| 5,823,950 A | | 10/1998 | Diab et al. |
| 5,823,952 A | | 10/1998 | Levinson et al. |
| 5,827,182 A | | 10/1998 | Raley et al. |
| 5,830,135 A | | 11/1998 | Bosque et al. |
| 5,830,136 A | | 11/1998 | DeLonzor et al. |
| 5,830,137 A | | 11/1998 | Scharf |
| 5,839,439 A | | 11/1998 | Nierlich et al. |
| RE36,000 E | | 12/1998 | Swedlow et al. |
| 5,842,979 A | | 12/1998 | Jarman et al. |
| 5,842,981 A | | 12/1998 | Larsen et al. |
| 5,842,982 A | | 12/1998 | Mannheimer |
| 5,846,190 A | | 12/1998 | Woehrle |
| 5,851,178 A | | 12/1998 | Aronow |
| 5,851,179 A | | 12/1998 | Ritson et al. |
| 5,853,364 A | | 12/1998 | Baker, Jr. et al. |
| 5,860,919 A | | 1/1999 | Kiani-Azarbayjany et al. |
| 5,865,736 A | | 2/1999 | Baker, Jr. et al. |
| 5,871,442 A | | 2/1999 | Madarasz et al. |
| 5,879,294 A | | 3/1999 | Anderson et al. |
| 5,885,213 A | | 3/1999 | Richardson et al. |
| 5,890,929 A | | 4/1999 | Mills et al. |
| 5,891,021 A | | 4/1999 | Dillon et al. |
| 5,891,022 A | | 4/1999 | Pologe |
| 5,891,024 A | | 4/1999 | Jarman et al. |
| 5,891,025 A | | 4/1999 | Buschmann et al. |
| 5,891,026 A | | 4/1999 | Wang et al. |
| 5,902,235 A | | 5/1999 | Lewis et al. |
| 5,910,108 A | | 6/1999 | Solenberger |
| 5,911,690 A | | 6/1999 | Rall |
| 5,912,656 A | | 6/1999 | Tham et al. |
| 5,913,819 A | | 6/1999 | Taylor et al. |
| 5,916,154 A | | 6/1999 | Hobbs et al. |
| 5,916,155 A | | 6/1999 | Levinson et al. |
| 5,919,133 A | | 7/1999 | Taylor et al. |
| 5,919,134 A | | 7/1999 | Diab |

| | | | | | | |
|---|---|---|---|---|---|---|
| 5,920,263 | A | 7/1999 | Huttenhoff et al. | 6,181,958 B1 | 1/2001 | Steuer et al. |
| 5,921,921 | A | 7/1999 | Potratz et al. | 6,181,959 B1 | 1/2001 | Schöllerman et al. |
| 5,922,607 | A | 7/1999 | Bernreuter | 6,184,521 B1 | 2/2001 | Coffin, IV et al. |
| 5,924,979 | A | 7/1999 | Swedlow et al. | 6,188,470 B1 | 2/2001 | Grace |
| 5,924,980 | A | 7/1999 | Coetzee | 6,192,260 B1 | 2/2001 | Chance |
| 5,924,982 | A | 7/1999 | Chin | 6,195,575 B1 | 2/2001 | Levinson |
| 5,924,985 | A | 7/1999 | Jones | 6,198,951 B1 | 3/2001 | Kosuda et al. |
| 5,934,277 | A | 8/1999 | Mortz | 6,206,830 B1 | 3/2001 | Diab et al. |
| 5,934,925 | A | 8/1999 | Tobler et al. | 6,213,952 B1 * | 4/2001 | Finarov et al. ................ 600/491 |
| 5,940,182 | A | 8/1999 | Lepper, Jr. et al. | 6,217,523 B1 | 4/2001 | Amano et al. |
| 5,954,644 | A | 9/1999 | Dettling et al. | 6,222,189 B1 | 4/2001 | Misner et al. |
| 5,960,610 | A | 10/1999 | Levinson et al. | 6,226,539 B1 | 5/2001 | Potratz |
| 5,961,450 | A | 10/1999 | Merchant et al. | 6,226,540 B1 | 5/2001 | Bernreuter et al. |
| 5,961,452 | A | 10/1999 | Chung et al. | 6,229,856 B1 | 5/2001 | Diab et al. |
| 5,964,701 | A | 10/1999 | Asada et al. | 6,230,035 B1 | 5/2001 | Aoyagi et al. |
| 5,971,930 | A | 10/1999 | Elghazzawi | 6,233,470 B1 | 5/2001 | Tsuchiya |
| 5,978,691 | A | 11/1999 | Mills | 6,236,871 B1 | 5/2001 | Tsuchiya |
| 5,978,693 | A | 11/1999 | Hamilton et al. | 6,236,872 B1 | 5/2001 | Diab et al. |
| 5,983,122 | A | 11/1999 | Jarman et al. | 6,240,305 B1 | 5/2001 | Tsuchiya |
| 5,987,343 | A | 11/1999 | Kinast | 6,253,097 B1 | 6/2001 | Aronow et al. |
| 5,991,648 | A | 11/1999 | Levin | 6,253,098 B1 | 6/2001 | Walker et al. |
| 5,995,855 | A | 11/1999 | Kiani et al. | 6,256,523 B1 | 7/2001 | Diab et al. |
| 5,995,856 | A | 11/1999 | Mannheimer et al. | 6,256,524 B1 | 7/2001 | Walker et al. |
| 5,995,858 | A | 11/1999 | Kinast | 6,261,236 B1 | 7/2001 | Grimblatov |
| 5,995,859 | A | 11/1999 | Takahashi | 6,263,221 B1 | 7/2001 | Chance et al. |
| 5,997,343 | A | 12/1999 | Mills et al. | 6,263,222 B1 | 7/2001 | Diab et al. |
| 5,999,834 | A | 12/1999 | Wang et al. | 6,263,223 B1 | 7/2001 | Sheperd et al. |
| 6,002,952 | A | 12/1999 | Diab et al. | 6,266,546 B1 | 7/2001 | Steuer et al. |
| 6,005,658 | A | 12/1999 | Kaluza et al. | 6,266,547 B1 | 7/2001 | Walker et al. |
| 6,006,120 | A | 12/1999 | Levin | 6,272,363 B1 | 8/2001 | Casciani et al. |
| 6,011,985 | A | 1/2000 | Athan et al. | 6,278,522 B1 | 8/2001 | Lepper, Jr. et al. |
| 6,011,986 | A | 1/2000 | Diab et al. | 6,280,213 B1 | 8/2001 | Tobler et al. |
| 6,014,576 | A | 1/2000 | Raley | 6,280,381 B1 | 8/2001 | Malin et al. |
| 6,018,673 | A | 1/2000 | Chin et al. | 6,285,894 B1 | 9/2001 | Oppelt et al. |
| 6,018,674 | A | 1/2000 | Aronow | 6,285,895 B1 * | 9/2001 | Ristolainen et al. .......... 600/323 |
| 6,022,321 | A | 2/2000 | Amano et al. | 6,285,896 B1 | 9/2001 | Tobler et al. |
| 6,023,541 | A | 2/2000 | Merchant et al. | 6,298,252 B1 | 10/2001 | Kovach et al. |
| 6,026,312 | A | 2/2000 | Shemwell et al. | 6,308,089 B1 | 10/2001 | Von der Ruhr et al. |
| 6,026,314 | A | 2/2000 | Amerov et al. | 6,321,100 B1 | 11/2001 | Parker |
| 6,031,603 | A | 2/2000 | Fine et al. | 6,330,468 B1 | 12/2001 | Scharf |
| 6,035,223 | A | 3/2000 | Baker, Jr. | 6,334,065 B1 | 12/2001 | Al-Ali et al. |
| 6,036,642 | A | 3/2000 | Diab et al. | 6,339,715 B1 | 1/2002 | Bahr et al. |
| 6,041,247 | A | 3/2000 | Weckstrom et al. | 6,343,223 B1 | 1/2002 | Chin et al. |
| 6,044,283 | A | 3/2000 | Fein et al. | 6,343,224 B1 | 1/2002 | Parker |
| 6,047,201 | A | 4/2000 | Jackson, III | 6,349,228 B1 | 2/2002 | Kiani et al. |
| 6,061,584 | A | 5/2000 | Lovejoy et al. | 6,351,658 B1 | 2/2002 | Middleman et al. |
| 6,064,898 | A | 5/2000 | Aldrich | 6,353,750 B1 | 3/2002 | Kimura et al. |
| 6,064,899 | A | 5/2000 | Fein et al. | 6,356,774 B1 | 3/2002 | Bernstein et al. |
| 6,067,462 | A | 5/2000 | Diab et al. | 6,360,113 B1 | 3/2002 | Dettling |
| 6,073,038 | A | 6/2000 | Wang et al. | 6,360,114 B1 | 3/2002 | Diab et al. |
| 6,078,833 | A | 6/2000 | Hueber | 6,361,501 B1 | 3/2002 | Amano et al. |
| 6,081,735 | A | 6/2000 | Diab et al. | 6,363,269 B1 | 3/2002 | Hanna et al. |
| 6,081,742 | A | 6/2000 | Amano et al. | 6,370,408 B1 | 4/2002 | Merchant et al. |
| 6,083,157 | A | 7/2000 | Noller | 6,370,409 B1 | 4/2002 | Chung et al. |
| 6,083,172 | A | 7/2000 | Baker, Jr. et al. | 6,374,129 B1 | 4/2002 | Chin et al. |
| 6,088,607 | A | 7/2000 | Diab et al. | 6,377,829 B1 | 4/2002 | Al-Ali |
| 6,094,592 | A | 7/2000 | Yorkey et al. | 6,381,479 B1 | 4/2002 | Norris |
| 6,095,974 | A | 8/2000 | Shemwell et al. | 6,381,480 B1 | 4/2002 | Stoddart et al. |
| 6,104,938 | A | 8/2000 | Huiku et al. | 6,385,471 B1 | 5/2002 | Mortz |
| 6,112,107 | A | 8/2000 | Hannula | 6,385,821 B1 | 5/2002 | Modgil et al. |
| 6,113,541 | A | 9/2000 | Dias et al. | 6,388,240 B2 | 5/2002 | Schulz et al. |
| 6,115,621 | A | 9/2000 | Chin | 6,393,310 B1 | 5/2002 | Kuenstner |
| 6,122,535 | A | 9/2000 | Kaestle et al. | 6,397,091 B2 | 5/2002 | Diab et al. |
| 6,133,994 | A | 10/2000 | Mathews et al. | 6,397,092 B1 | 5/2002 | Norris et al. |
| 6,135,952 | A | 10/2000 | Coetzee | 6,397,093 B1 | 5/2002 | Aldrich |
| 6,144,444 | A | 11/2000 | Haworth et al. | 6,400,971 B1 | 6/2002 | Finarov et al. |
| 6,144,867 | A | 11/2000 | Walker et al. | 6,400,972 B1 | 6/2002 | Fine |
| 6,144,868 | A | 11/2000 | Parker | 6,402,690 B1 | 6/2002 | Rhee et al. |
| 6,149,481 | A | 11/2000 | Wang et al. | 6,408,198 B1 | 6/2002 | Hanna et al. |
| 6,150,951 | A | 11/2000 | Olejniczak | 6,411,832 B1 | 6/2002 | Guthermann |
| 6,151,107 | A | 11/2000 | Schöllerman et al. | 6,411,833 B1 | 6/2002 | Baker, Jr. et al. |
| 6,151,518 | A | 11/2000 | Hayashi | 6,419,671 B1 | 7/2002 | Lemberg |
| 6,152,754 | A | 11/2000 | Gerhardt et al. | 6,421,549 B1 | 7/2002 | Jacques |
| 6,154,667 | A | 11/2000 | Miura et al. | 6,430,423 B2 | 8/2002 | DeLonzor et al. |
| 6,157,850 | A | 12/2000 | Diab et al. | 6,430,513 B1 | 8/2002 | Wang et al. |
| 6,163,715 | A | 12/2000 | Larsen et al. | 6,430,525 B1 | 8/2002 | Weber et al. |
| 6,165,005 | A | 12/2000 | Mills et al. | 6,434,408 B1 | 8/2002 | Heckel et al. |
| 6,173,196 | B1 | 1/2001 | Delonzor et al. | 6,438,399 B1 | 8/2002 | Kurth |
| 6,178,343 | B1 | 1/2001 | Bindszus et al. | 6,449,501 B1 | 9/2002 | Reuss |

| | | |
|---|---|---|
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 * | 1/2003 | Larson ......................... 600/323 |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 * | 4/2003 | Schulz et al. .................. 250/221 |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |

| Patent | Date | Name | Ref |
|---|---|---|---|
| 6,839,659 B2 | 1/2005 | Tarassenko et al. | |
| 6,842,635 B1 | 1/2005 | Parker | |
| 6,845,256 B2 | 1/2005 | Chin et al. | |
| 6,850,787 B2 | 2/2005 | Weber et al. | |
| 6,850,788 B2 | 2/2005 | Al-Ali | |
| 6,850,789 B2 | 2/2005 | Schweitzer, Jr. et al. | |
| 6,861,639 B2 | 3/2005 | Al-Ali | |
| 6,863,652 B2 | 3/2005 | Huang et al. | |
| 6,865,407 B2 | 3/2005 | Kimball et al. | |
| 6,879,850 B2 | 4/2005 | Kimball | |
| 6,882,874 B2 | 4/2005 | Huiku | |
| 6,889,153 B2 | 5/2005 | Dietiker | |
| 6,898,452 B2 | 5/2005 | Al-Ali et al. | |
| 6,909,912 B2 | 6/2005 | Melker | |
| 6,912,413 B2 | 6/2005 | Rantala et al. | |
| 6,916,289 B2 | 7/2005 | Schnall | |
| 6,920,345 B2 * | 7/2005 | Al-Ali et al. | 600/344 |
| 6,931,269 B2 | 8/2005 | Terry | |
| 6,934,570 B2 | 8/2005 | Kiani et al. | |
| 6,939,307 B1 | 9/2005 | Dunlop | |
| 6,941,162 B2 | 9/2005 | Fudge et al. | |
| 6,947,781 B2 | 9/2005 | Asada et al. | |
| 6,950,687 B2 | 9/2005 | Al-Ali | |
| 6,963,767 B2 | 11/2005 | Rantala et al. | |
| 6,971,580 B2 | 12/2005 | Zhu et al. | |
| 6,983,178 B2 * | 1/2006 | Fine et al. | 600/335 |
| 6,985,763 B2 | 1/2006 | Boas et al. | |
| 6,985,764 B2 | 1/2006 | Mason et al. | |
| 6,990,426 B2 | 1/2006 | Yoon et al. | |
| 6,992,751 B2 | 1/2006 | Okita et al. | |
| 6,992,772 B2 | 1/2006 | Block et al. | |
| 6,993,371 B2 | 1/2006 | Kiani et al. | |
| 6,993,372 B2 * | 1/2006 | Fine et al. | 600/335 |
| 6,996,427 B2 | 2/2006 | Ali et al. | |
| 7,003,338 B2 | 2/2006 | Weber et al. | |
| 7,003,339 B2 | 2/2006 | Diab et al. | |
| 7,006,855 B1 | 2/2006 | Sarussi | |
| 7,006,856 B2 | 2/2006 | Baker, Jr. et al. | |
| 7,016,715 B2 | 3/2006 | Stetson | |
| 7,020,507 B2 | 3/2006 | Scharf et al. | |
| 7,024,233 B2 | 4/2006 | Ali et al. | |
| 7,024,235 B2 | 4/2006 | Melker et al. | |
| 7,025,728 B2 | 4/2006 | Ito et al. | |
| 7,027,849 B2 | 4/2006 | Al-Ali et al. | |
| 7,027,850 B2 | 4/2006 | Wasserman | |
| 7,035,697 B1 | 4/2006 | Brown | |
| 7,039,449 B2 | 5/2006 | Al-Ali | |
| 7,043,289 B2 | 5/2006 | Fine et al. | |
| 7,047,055 B2 | 5/2006 | Boaz et al. | |
| 7,047,056 B2 | 5/2006 | Hannula et al. | |
| 7,060,035 B2 | 6/2006 | Wasserman et al. | |
| 7,062,307 B2 | 6/2006 | Norris et al. | |
| 7,067,893 B2 | 6/2006 | Mills et al. | |
| 7,072,701 B2 | 7/2006 | Chen et al. | |
| 7,072,702 B2 | 7/2006 | Edgar, Jr. et al. | |
| 7,079,880 B2 | 7/2006 | Stetson | |
| 7,085,597 B2 | 8/2006 | Fein et al. | |
| 7,096,052 B2 | 8/2006 | Mason et al. | |
| 7,096,054 B2 | 8/2006 | Abdul-Hafiz et al. | |
| 7,107,088 B2 | 9/2006 | Aceti | |
| 7,113,815 B2 | 9/2006 | O'Neil et al. | |
| 7,123,950 B2 | 10/2006 | Mannheimer | |
| 7,127,278 B2 | 10/2006 | Melker et al. | |
| 7,130,671 B2 | 10/2006 | Baker, Jr. et al. | |
| 7,132,641 B2 | 11/2006 | Schulz et al. | |
| 7,133,711 B2 | 11/2006 | Chernoguz et al. | |
| 7,139,559 B2 | 11/2006 | Kenagy et al. | |
| 7,142,901 B2 | 11/2006 | Kiani et al. | |
| 7,162,288 B2 | 1/2007 | Nordstrom | |
| 7,190,987 B2 | 3/2007 | Lindekugel et al. | |
| 7,198,778 B2 | 4/2007 | Achilefu et al. | |
| 7,209,775 B2 | 4/2007 | Bae et al. | |
| 7,215,984 B2 | 5/2007 | Diab et al. | |
| 7,225,006 B2 | 5/2007 | Al-Ali et al. | |
| 7,236,811 B2 | 6/2007 | Schmitt | |
| 7,236,881 B2 | 6/2007 | Liu et al. | |
| 7,248,910 B2 | 7/2007 | Li et al. | |
| 7,254,433 B2 | 8/2007 | Diab et al. | |
| 7,254,434 B2 | 8/2007 | Schulz et al. | |
| 7,263,395 B2 * | 8/2007 | Chan et al. | 600/335 |
| 7,272,426 B2 | 9/2007 | Scmid | |
| 7,280,858 B2 | 10/2007 | Al-Ali et al. | |
| 7,295,866 B2 | 11/2007 | Al-Ali | |
| 7,305,262 B2 | 12/2007 | Brodnick et al. | |
| 7,315,753 B2 | 1/2008 | Baker, Jr. et al. | |
| 7,412,272 B2 * | 8/2008 | Medina | 600/344 |
| 7,734,321 B2 * | 6/2010 | White | 600/310 |
| 7,937,129 B2 * | 5/2011 | Mason et al. | 600/323 |
| 2001/0021803 A1 | 9/2001 | Blank et al. | |
| 2001/0051767 A1 | 12/2001 | Williams et al. | |
| 2002/0026109 A1 | 2/2002 | Diab et al. | |
| 2002/0028990 A1 | 3/2002 | Sheperd et al. | |
| 2002/0038078 A1 | 3/2002 | Ito | |
| 2002/0042558 A1 | 4/2002 | Mendelson | |
| 2002/0068859 A1 | 6/2002 | Knopp | |
| 2002/0128544 A1 | 9/2002 | Diab et al. | |
| 2002/0133067 A1 | 9/2002 | Jackson, III | |
| 2002/0156354 A1 | 10/2002 | Larson | |
| 2002/0173706 A1 | 11/2002 | Takatani | |
| 2002/0173709 A1 | 11/2002 | Fine et al. | |
| 2002/0190863 A1 | 12/2002 | Lynn | |
| 2002/0198442 A1 | 12/2002 | Rantala et al. | |
| 2003/0018243 A1 | 1/2003 | Gerhardt et al. | |
| 2003/0036690 A1 | 2/2003 | Geddes et al. | |
| 2003/0045785 A1 | 3/2003 | Diab et al. | |
| 2003/0073889 A1 | 4/2003 | Keilbach et al. | |
| 2003/0073890 A1 | 4/2003 | Hanna | |
| 2003/0100840 A1 | 5/2003 | Sugiura et al. | |
| 2003/0132495 A1 | 7/2003 | Mills et al. | |
| 2003/0135099 A1 | 7/2003 | Al-Ali | |
| 2003/0162414 A1 | 8/2003 | Schulz et al. | |
| 2003/0171662 A1 | 9/2003 | O'Connor et al. | |
| 2003/0176776 A1 | 9/2003 | Huiku | |
| 2003/0181799 A1 | 9/2003 | Lindekugel et al. | |
| 2003/0187337 A1 | 10/2003 | Tarassenko et al. | |
| 2003/0195402 A1 | 10/2003 | Fein et al. | |
| 2003/0197679 A1 | 10/2003 | Ali et al. | |
| 2003/0212316 A1 | 11/2003 | Leiden et al. | |
| 2003/0225323 A1 | 12/2003 | Kiani et al. | |
| 2003/0225337 A1 | 12/2003 | Scharf et al. | |
| 2003/0236452 A1 | 12/2003 | Melker et al. | |
| 2003/0236647 A1 | 12/2003 | Yoon et al. | |
| 2004/0006261 A1 | 1/2004 | Swedlow et al. | |
| 2004/0010188 A1 | 1/2004 | Wasserman et al. | |
| 2004/0024297 A1 | 2/2004 | Chen et al. | |
| 2004/0024326 A1 | 2/2004 | Yeo et al. | |
| 2004/0034293 A1 | 2/2004 | Kimball | |
| 2004/0039272 A1 | 2/2004 | Abdul-Hafiz et al. | |
| 2004/0039273 A1 | 2/2004 | Terry | |
| 2004/0054269 A1 | 3/2004 | Rantala et al. | |
| 2004/0054291 A1 | 3/2004 | Schulz et al. | |
| 2004/0059209 A1 | 3/2004 | Al-Ali et al. | |
| 2004/0059210 A1 | 3/2004 | Stetson | |
| 2004/0064020 A1 | 4/2004 | Diab et al. | |
| 2004/0068164 A1 | 4/2004 | Diab et al. | |
| 2004/0087846 A1 | 5/2004 | Wasserman | |
| 2004/0092805 A1 | 5/2004 | Yarita | |
| 2004/0097797 A1 | 5/2004 | Porges et al. | |
| 2004/0098009 A1 | 5/2004 | Boecker et al. | |
| 2004/0107065 A1 | 6/2004 | Al-Ali et al. | |
| 2004/0116788 A1 | 6/2004 | Chernoguz et al. | |
| 2004/0116789 A1 | 6/2004 | Boaz et al. | |
| 2004/0117891 A1 | 6/2004 | Hannula et al. | |
| 2004/0122300 A1 | 6/2004 | Boas et al. | |
| 2004/0122302 A1 | 6/2004 | Mason et al. | |
| 2004/0133087 A1 | 7/2004 | Ali et al. | |
| 2004/0133088 A1 | 7/2004 | Al-Ali et al. | |
| 2004/0138538 A1 | 7/2004 | Stetson | |
| 2004/0138540 A1 | 7/2004 | Baker, Jr. et al. | |
| 2004/0143172 A1 | 7/2004 | Fudge et al. | |
| 2004/0147821 A1 | 7/2004 | Al-Ali et al. | |
| 2004/0147822 A1 | 7/2004 | Al-Ali et al. | |
| 2004/0147823 A1 | 7/2004 | Kiani et al. | |
| 2004/0147824 A1 | 7/2004 | Diab et al. | |
| 2004/0152965 A1 | 8/2004 | Diab et al. | |
| 2004/0158134 A1 | 8/2004 | Diab et al. | |
| 2004/0158135 A1 | 8/2004 | Baker, Jr. et al. | |
| 2004/0162472 A1 | 8/2004 | Berson et al. | |

| | | | |
|---|---|---|---|
| 2004/0171920 A1 | 9/2004 | Mannheimer et al. | |
| 2004/0171948 A1 | 9/2004 | Terry | |
| 2004/0176671 A1 | 9/2004 | Fine et al. | |
| 2004/0181133 A1 | 9/2004 | Al-Ali et al. | |
| 2004/0181134 A1 | 9/2004 | Baker, Jr. et al. | |
| 2004/0186358 A1 | 9/2004 | Chernow et al. | |
| 2004/0199063 A1 | 10/2004 | O'Neil et al. | |
| 2004/0204636 A1 | 10/2004 | Diab et al. | |
| 2004/0204637 A1 | 10/2004 | Diab et al. | |
| 2004/0204638 A1 | 10/2004 | Diab et al. | |
| 2004/0204639 A1 | 10/2004 | Casciani et al. | |
| 2004/0204865 A1 | 10/2004 | Lee et al. | |
| 2004/0210146 A1 | 10/2004 | Diab et al. | |
| 2004/0215069 A1 | 10/2004 | Mannheimer | |
| 2004/0230107 A1 | 11/2004 | Asada et al. | |
| 2004/0230108 A1 | 11/2004 | Melker et al. | |
| 2004/0236196 A1 | 11/2004 | Diab et al. | |
| 2004/0242980 A1 | 12/2004 | Kiani et al. | |
| 2004/0249252 A1 | 12/2004 | Fine et al. | |
| 2004/0257557 A1 | 12/2004 | Block et al. | |
| 2004/0260161 A1 | 12/2004 | Melker et al. | |
| 2004/0267103 A1 | 12/2004 | Li et al. | |
| 2004/0267104 A1 | 12/2004 | Hannula et al. | |
| 2004/0267140 A1 | 12/2004 | Ito et al. | |
| 2005/0004479 A1 | 1/2005 | Townsend et al. | |
| 2005/0010092 A1 | 1/2005 | Weber et al. | |
| 2005/0020887 A1 | 1/2005 | Goldberg | |
| 2005/0020894 A1 | 1/2005 | Norris et al. | |
| 2005/0033128 A1 | 2/2005 | Ali et al. | |
| 2005/0033129 A1 | 2/2005 | Edgar, Jr. et al. | |
| 2005/0043599 A1 | 2/2005 | O'Mara | |
| 2005/0043600 A1 | 2/2005 | Diab et al. | |
| 2005/0049470 A1 | 3/2005 | Terry | |
| 2005/0049471 A1 | 3/2005 | Aceti | |
| 2005/0075550 A1 | 4/2005 | Lindekugel | |
| 2005/0113651 A1 | 5/2005 | Wood et al. | |
| 2005/0177034 A1 | 8/2005 | Beaumont | |
| 2005/0197548 A1 | 9/2005 | Dietiker | |
| 2005/0228248 A1 | 10/2005 | Dietiker | |
| 2005/0272986 A1* | 12/2005 | Smith et al. | 600/310 |
| 2005/0277819 A1 | 12/2005 | Kiani et al. | |
| 2005/0283059 A1 | 12/2005 | Iyer et al. | |
| 2006/0009685 A1* | 1/2006 | Finarov et al. | 600/310 |
| 2006/0058594 A1 | 3/2006 | Ishizuka et al. | |
| 2006/0084852 A1 | 4/2006 | Mason et al. | |
| 2006/0089547 A1 | 4/2006 | Sarussi | |
| 2006/0106294 A1 | 5/2006 | Maser et al. | |
| 2006/0129040 A1* | 6/2006 | Fine et al. | 600/335 |
| 2006/0195028 A1 | 8/2006 | Hannula et al. | |
| 2006/0224058 A1 | 10/2006 | Mannheimer | |
| 2006/0247501 A1 | 11/2006 | Ali | |
| 2006/0258921 A1 | 11/2006 | Addison et al. | |
| 2006/0276700 A1 | 12/2006 | O'Neil et al. | |
| 2007/0032710 A1 | 2/2007 | Raridan et al. | |
| 2007/0032712 A1 | 2/2007 | Raridan et al. | |
| 2007/0032713 A1 | 2/2007 | Eghbal et al. | |
| 2007/0032715 A1 | 2/2007 | Eghbal et al. | |
| 2007/0032716 A1 | 2/2007 | Raridan et al. | |
| 2007/0073121 A1 | 3/2007 | Hoarau et al. | |
| 2007/0073125 A1 | 3/2007 | Hoarau et al. | |
| 2007/0073126 A1 | 3/2007 | Raridan, Jr. | |
| 2007/0073128 A1 | 3/2007 | Hoarau et al. | |
| 2007/0123763 A1* | 5/2007 | Al-Ali et al. | 600/344 |
| 2007/0260131 A1* | 11/2007 | Chin | 600/323 |
| 2009/0143842 A1* | 6/2009 | Cumbie et al. | 607/88 |

FOREIGN PATENT DOCUMENTS

| | | |
|---|---|---|
| DE | 3703458 | 8/1988 |
| DE | 19632361 | 2/1997 |
| EP | 0127947 | 12/1984 |
| EP | 0204259 | 12/1986 |
| EP | 0531631 | 3/1993 |
| EP | 0724860 | 8/1996 |
| EP | 1945099 | 7/2008 |
| FR | 2685865 | 7/1993 |
| JP | 7001273 | 11/1987 |
| JP | 2111343 | 4/1990 |
| JP | 5049625 | 3/1993 |
| JP | 6014906 | 1/1994 |
| JP | 6269430 | 9/1994 |
| JP | 3116259 | 6/1995 |
| JP | 3116260 | 6/1995 |
| JP | 7236625 | 9/1995 |
| JP | 10216115 | 8/1998 |
| JP | 10337282 | 12/1998 |
| JP | 2000237170 | 9/2000 |
| JP | 2003275192 | 9/2003 |
| JP | 2004089546 | 3/2004 |
| JP | 2004248820 | 9/2004 |
| JP | 2004329406 | 11/2004 |
| JP | 2004337605 | 12/2004 |
| JP | 2004344367 | 12/2004 |
| JP | 2004351107 | 12/2004 |
| WO | WO8909566 | 10/1989 |
| WO | WO9111137 | 8/1991 |
| WO | WO9221281 | 12/1992 |
| WO | WO9502358 | 1/1995 |
| WO | WO9736536 | 10/1997 |
| WO | WO9857577 | 12/1998 |
| WO | WO9947039 | 9/1999 |
| WO | 0059374 | 10/2000 |
| WO | WO0059374 | 10/2000 |
| WO | WO2005010567 | 2/2005 |
| WO | WO2005010568 | 2/2005 |

OTHER PUBLICATIONS

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Irie, A., et al.; "Respiration Monitors—Pulse Oximeters," *Neonatal Care*, vol. 15, No. 12, pp. 78-83 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

http://www.fcw.com.my/fujifilm.html.

\* cited by examiner

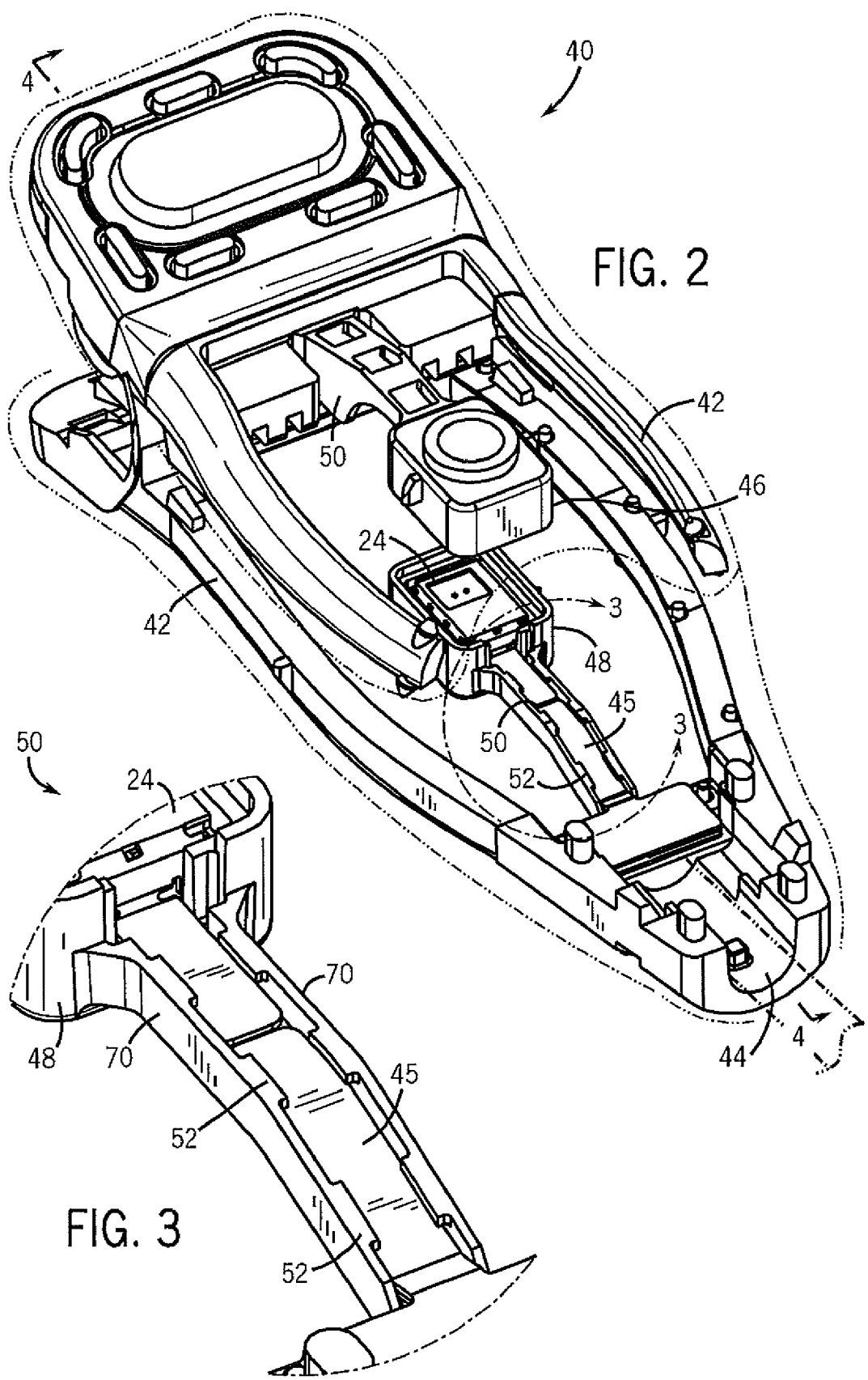

FLEX CIRCUIT SNAP TRACK FOR A BIOMETRIC SENSOR

RELATED APPLICATION

This application claims priority from U.S. Patent Application No. 61/009,676 which was filed on Dec. 31, 2007 and is incorporated herein by reference in its entirety.

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

Pulse oximetry sensors may include a flex circuit that electrically connects various electrical components of the sensor. For example, components of the flex circuit may include an optical emitter, such as an LED, a photodetector and wires forming conductors which electrically connect the sensor components and/or allow connection of the sensor components to a pulse oximeter monitor. During fabrication of such a sensor, various aspects of the manufacturing process may place mechanical stresses upon the flex circuit or the attached components such that the circuit and/or components are moved from their desired positions, resulting in a sensor being fabricated in which the flex circuit and/or electrical components are displaced and/or misaligned with respect to the remainder of the sensor body, potentially rendering the sensor unusable.

SUMMARY

Certain aspects commensurate in scope with the disclosure are set forth below. It should be understood that these aspects are presented merely to provide the reader with a brief summary of embodiments and that these aspects are not intended to limit the scope of the disclosure. Indeed, the disclosure may encompass a variety of aspects that may not be set forth below.

In an embodiment, there is provided a sensor frame. The sensor frame includes a frame body configured to house one or more optical components. The sensor body further includes one or more retaining features provided on the frame body, such that the one or more retaining features are configured to limit the movement of a flex circuit electrically connected to the one or more optical components.

In an embodiment, there is provided a sensor assembly. The sensor assembly includes a light emitting component and a photodetecting component. The sensor assembly further comprise a flex circuit connecting at least the light emitting component and the light detecting component, and a frame comprising one or more retaining features configured to restrict movement of at least part of the flex circuit.

In an embodiment there is provided a method for manufacturing a sensor. The method includes positioning a flex circuit on a frame such that retaining features on at least part of the frame restrict the motion of the flex circuit. The method further includes the act of coating the frame.

BRIEF DESCRIPTION OF THE DRAWINGS

Advantages of the disclosure may become apparent upon reading the following detailed description and upon reference to the drawings in which:

FIG. 2 illustrates a perspective view of an internal frame for use in a patient sensor, in accordance with an embodiment;

FIG. 3 illustrates a blow-up view of the internal frame of FIG. 2, in accordance with an embodiment.

DETAILED DESCRIPTION OF SPECIFIC EMBODIMENTS

Figure 1:
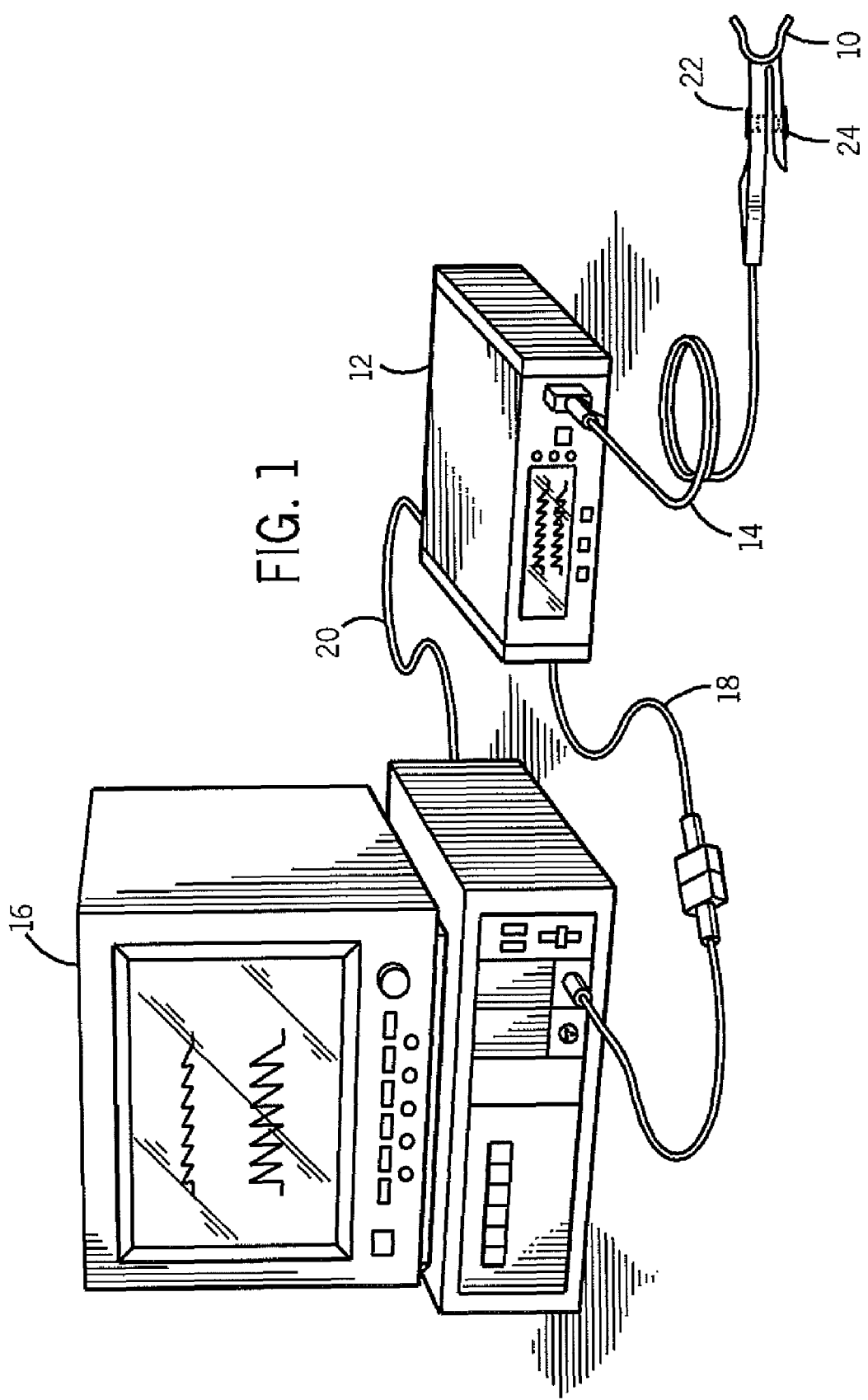
FIG. 1 illustrates a patient monitoring system coupled to a multi-parameter patient monitor and a sensor; in accordance with an embodiment.

Various embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In various embodiments, methods and systems for securing a flex circuit during a sensor fabrication process may be described. In one embodiment, the flex circuit is secured within a corresponding flex circuit track of a sensor frame. In such an embodiment, the sensor frame may be overmolded or otherwise used in the further construction of a sensor, such as a pulse oximetry sensor, without the flex circuit or attached electrical components becoming displaced or misaligned.

Prior to discussing embodiments of sensors in detail, it should be appreciated that such sensors are typically designed for use with a patient monitoring system. In various embodiments, referring now to FIG. 1, a sensor 10 according to the present disclosure may be used in conjunction with a patient monitor 12. In the depicted embodiment a cable 14 connects the sensor 10 to the patient monitor 12. As will be appreciated, the sensor 10 and/or the cable 14 may include or incorporate one or more integrated circuit devices or electrical devices, such as a memory, processor chip, or resistor, that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors.

In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or corresponding wireless transmissions) are typically used to transmit control or timing signals from the monitor 12 to the sensor 10 and/or to transmit acquired data from the sensor 10 to the monitor 12. In some embodiments, however, the cable 14 may be an optical fiber that allows optical signals to be conducted between the monitor 12 and the sensor 10.

In an embodiment, the patient monitor 12 may be a suitable pulse oximeter, such as those available from Nellcor Puritan Bennett LLC. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, is a clip-style sensor that is overmolded to provide a generally unitary or enclosed assembly. In various embodiments, the sensor 10 may include an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and detector 24 of the sensor 10. The cable 14 may be permanently coupled to the sensor 10, or it may be removably coupled to the sensor 10—the latter alternative being more useful and cost efficient in situations where the sensor 10 is disposable.

For pulse oximetry embodiments, the oxygen saturation of the patient's arterial blood may be determined using two or more wavelengths of light, most commonly red and near infrared wavelengths. Similarly, in other embodiments a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

In various embodiments, the overmolded sensor 10 discussed herein may be configured for either transmission or reflectance type sensing. Furthermore, the sensor 10 may include various structural and functional features designed to facilitate its use. An example of such a sensor and its use and construction may be found in U.S. application Ser. No. 11/199,524 titled "Medical Sensor and Technique for Using the Same" and filed on Aug. 8, 2005, which is hereby incorporated by reference in its entirety for all purposes. As will be appreciated by those of ordinary skill in the art, however, such discussion is merely an example and is not intended to limit the scope of the present disclosure.

Referring now to FIG. 2, an internal frame 40 of the sensor 10 is depicted in accordance with an embodiment. In the depicted example, the internal frame 40 is a skeletal frame for the sensor 10. In certain embodiments, the internal frame 40 may be constructed, in whole or in part, from polymeric materials, such as thermoplastics, capable of providing a suitable rigidity or semi-rigidity for the different portions of the internal frame 40. Examples of such suitable materials may include polypropylene and nylon, though other polymeric materials may also be suitable. For example, in one embodiment, the internal frame 40 is constructed from polyurethane having a durometer of 65 Shore D. In other embodiments, the internal frame 40 may be constructed, in whole or in part, from other suitably rigid or semi-rigid materials, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the internal frame 40.

In various embodiments, the internal frame 40 may be constructed as an integral structure or as a composite structure. For example, in one embodiment, the internal frame 40 may be constructed as a single piece from a single material or from different materials. Alternatively, the internal frame 40 may be constructed or assembled from two or more parts that are separately formed. In such embodiments, the different parts may be formed from the same or different materials. For example, in implementations where different parts are formed from different materials, each part may be constructed from a material having suitable mechanical and/or chemical properties for that part. The different parts may then be joined or fitted together to form the internal frame 40.

In various embodiments, the internal frame 40 may include different structures or regions that may or may not have similar rigidities. For example, the depicted skeletal frame includes top and bottom structural supports 42 that define the general shape of the sensor 10 when coated with an overmolding. In view of their structure providing function, the structural supports 42 may be constructed to be substantially rigid or semi-rigid. In addition, the skeletal frame may include a cable guide 44 through which a cable, such as an electrical or optical cable, may pass to connect to electrical or optical conductors formed on a flex circuit 45 attached to the emitter 22 and/or detector 24 upon assembly. For example, in one embodiment the emitter 22 and/or detector 24 and associated conductors may form components of the flex circuit 45 disposed on the frame 40.

In addition, in the depicted embodiment, the internal frame 40 may include component housings, such as the emitter housing 46 and detector housing 48, as well as one or more retaining features, such as struts 50 configured to couple such housings to the remainder of the flame 40. In one embodiment, such housings 46, 48 and struts 50, along with other components as discussed herein, may form a flex circuit track configured to secure and support the flex circuit on the frame 40.

For example, FIG. 3 (taken along circular region 3 in FIG. 2) is a blow-up view of one of the retaining features, i.e., struts 50, capable of securing a flex circuit 45. In this embodiment, the depicted strut 50 is adapted to secure the flex circuit 45 that electrically connects the detector 24, housed in detector housing 48, to additional elements of the flex circuit 45. In the depicted embodiment of FIG. 3, side panels 70 are depicted that extend along the outer edges of the strut 50, defining its outer boundaries. Disposed on the upper edge of the side panels 70 are tabs 52, extending inward from the side panels 70.

As will be appreciated, the flex circuit 45 may be placed in the track formed by the sidewalls 70 and the tabs 52 by snap fitting, i.e., applying pressure to the flex circuit 45 such that the flex circuit 45 bends or gives sufficiently along its edges to allow the flex circuit 45 to move past the tabs 52. Therefore, the tabs 52 may be sized such that the flexibility of the flex circuit 45 is sufficient to allow the flex circuit 45 to be pressed or snap fit past the tabs 52. Alternatively, the flex circuit 45 may be tilted or angled to facilitate moving the flex circuit 45 past the tabs 52 initially.

In the illustrated embodiment, the tabs 52 are flush with the upper surface of the side panel 70 and have a thickness that is equal to or less than the thickness of the side panels 70 and/or the one or more retaining features, i.e., the strut 50. As will be appreciated by those of ordinary skill in the art, in other embodiments the thickness and placement of the tabs 52 may vary. For example, in the illustrated embodiment the tabs 52 are disposed periodically along the side panels 70 and the tabs 52 are of similar or equal length. However, in other embodiments the lengths of the tabs 52 may vary depending on their placement along the side panels 70. Likewise, the tabs need not be spaced regularly or periodically, but may instead be placed to at locations on the strut 50 where they will be suitably effective at retaining the flex circuit 45 on the strut 50.

In various embodiments, the inward extension of the tabs 52 from the side panels 70 facilitates maintaining the flex circuit 45 on the retaining feature, i.e., strut 50, particularly during fabrication steps which might otherwise move or displace the flex circuit 45 from the frame 40. For example, in one embodiment, the tabs 52 and/or sidewalls 70 act to prevent the pressures arising during an overmolding process from dislodging the flex circuit 45 from the struts 50. In such an implementation, the depicted tabs 52 and sidewalls 70 of the internal frame 40 may help prevent the flex circuit 45 from being displaced by the high pressures when overmolding material is injected or cast onto the frame 40.

During such overmolding processes, the internal frame 40 may be positioned within a die or mold of the desired shape for the sensor 10. In one embodiment, a molten or otherwise unset overmold material may then be injected into the die or mold. Such injection may be done such that the overmolding material enters the die or mold at high speed subjecting the frame 40 to high pressures and strains. Accordingly, the retaining features (i.e., the sidewalls 70 and/or the tabs 52) of the struts 50 ensure that the flex circuit 45 remains properly oriented on the frame 40 during the overmolding process. Likewise, in some embodiments, the overmold material may be injected in to the mold at high temperatures, such as between about 400° F. to about 450° F. In such embodiments, the overmold material may then be set, such as by cooling for one or more minutes or by chemical treatment, to form the sensor body about the internal frame 40. Such an overmolding process may result in thermal expansions and contractions of the frame 40 and surrounding overmolding material. Accordingly, any potential movement and/or misalignment of the flex circuit 45 relative to the frame 40 can be mitigated or prevented by the retaining features of the struts 50 which secure the flex circuit 45 to the frame 40.

As will be appreciated, the injection molding process described herein is merely one technique by which the frame 40 may be coated to form a sensor body, with or without associated sensing components. Other techniques which may be employed include, but are not limited to, dipping the frame 40 into a molten or otherwise unset coating material to coat the frame 40 or spraying the frame 40 with a molten or otherwise unset coating material to coat the frame 40. In such implementations, the coating material may be subsequently set, such as by cooling or chemical means, to form the coating. Such alternative techniques, to the extent that they may result in the movement of the flex circuit 45 away from the frame 40, may also benefit from the use of the tabs 52 and/or sidewalls 70 on the frame 40, as described herein.

Figure 4:
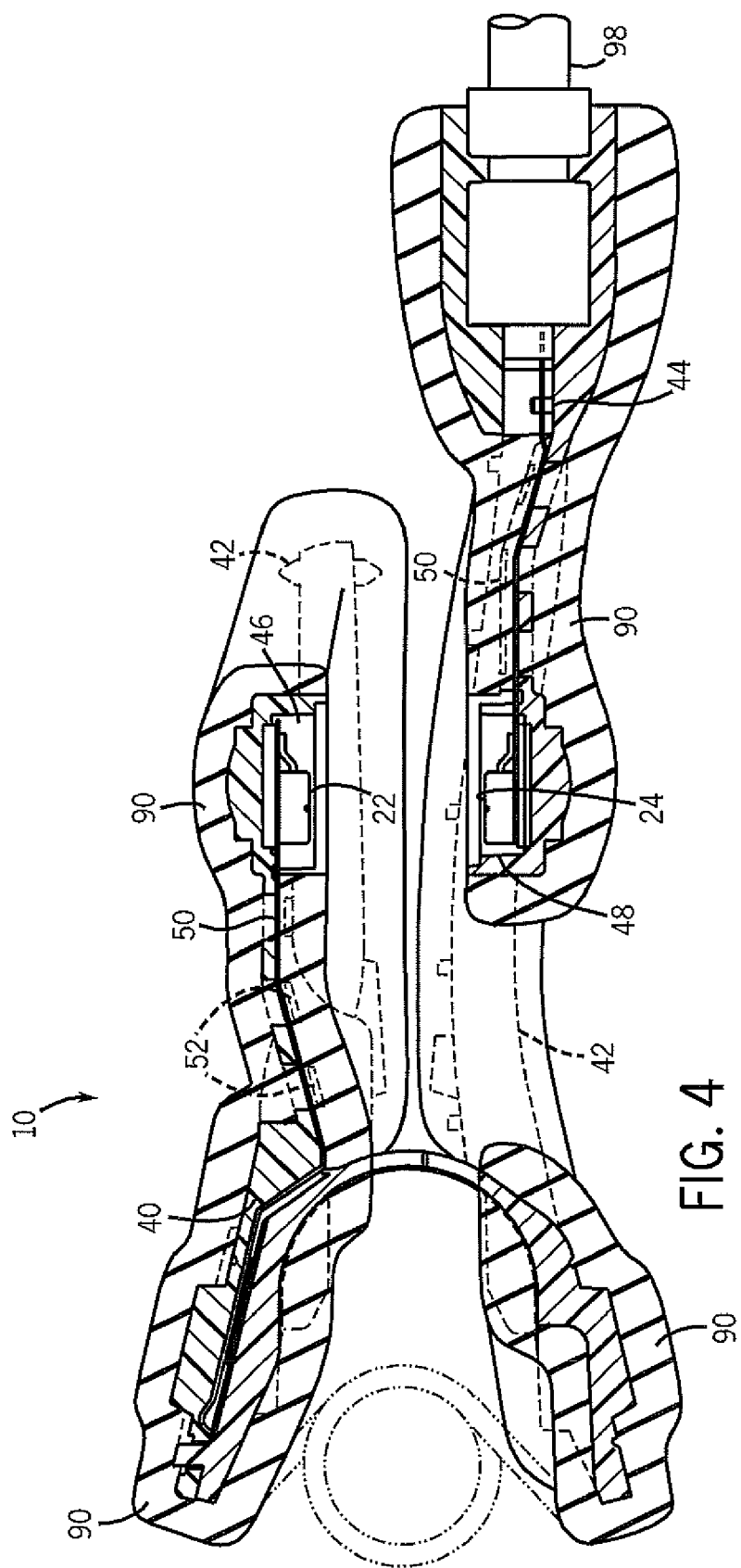
FIG. 4 illustrates a cross section view of an overmolded patient sensor, in accordance with an embodiment.

Turning now to FIG. 4, a cross-sectional view of the sensor 10 taken along line 4 of FIG. 2 is depicted in accordance with an embodiment. The figure depicts the sensor 10 coated with overmolding 90 covering the skeletal frame 40. In one embodiment, the overmolding 90 of the sensor 10 may be formed by an injection molding process, as described herein. Likewise, in certain embodiments, the frame 40 is coated to form a unitary or integral sensor assembly, as depicted in FIG. 4. Such an overmolded embodiment may result in a sensor assembly in which the internal frame 40 is completely or substantially coated.

In various embodiments, various overmolding processes of the sensor 10 may subject the flex circuit 45 to stresses and pressures such that the flex circuit 45 may dislodge from its designated position within the frame 40 and/or become damaged as a result of the overmolding process. Accordingly, the retaining features, such as the struts 50, may retain the flex circuit 45 on the frame 40 so that the overmolded sensor 10, such as the one shown in FIG. 4, may securely house the flex circuit 45 and components connected thereto.

Furthering the embodiment depicted in FIG. 4, a cable 98 may be disposed along cable guide 44 of the sensor 10 to connect the flex circuit 45 of the sensor 10 to an external device, such as the monitor 12 of FIG. 1, for use of the sensor 10. The cable 98 may join the flex circuit 45 at contact points disposed within the sensor 10. In the illustrated embodiment, the cable 98 is partially coated with the overmolding 90 so that it is securely affixed to the sensor 10.

While the medical sensors 10 discussed herein are some examples of overmolded or coated medical devices, other such devices are also contemplated and fall within the scope of the present disclosure. For example, other medical sensors and/or contacts applied externally to a patient may be advantageously applied using an overmolded sensor body having flex circuitry retaining features as discussed herein. For example, devices for measuring tissue water fraction or other body fluid related metrics may utilize a sensor as described herein. Likewise, other spectrophotometric applications where a probe is attached to a patient may utilize a sensor as described herein.

While the disclosure may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosure as defined by the following appended claims.

What is claimed is:

1. A sensor frame, comprising:
    a rigid or semi-rigid frame body capable of housing one or more optical components; and
    one or more retaining features provided on the frame body, wherein the one or more retaining features are disposed along a substantially continuous length of the frame body corresponding to substantially the entire length of a flex circuit and wherein the one or more retaining features generally limit movement along the length of the flex circuit relative to the frame body.

2. The sensor frame of claim 1, wherein the one or more retaining features comprise a pair of sidewalls disposed along at least a portion of the frame body.

3. The sensor frame of claim 2, wherein the one or more retaining features comprise the pair of sidewalls with two or more tabs disposed thereon.

4. The sensor frame of claim 1, wherein the frame body has a durometer of at least 65 Shore D.

5. The sensor frame of claim 1, wherein the frame body comprises polypropylene, nylon, polyurethane, stainless steel, aluminum, magnesium, graphite, fiberglass, or other metal alloy.

* * * * *